United States Patent [19]

Lemon et al.

[11] Patent Number: 5,112,226
[45] Date of Patent: May 12, 1992

[54] CONSTANT PRESSURE PERIODONTAL PROBE

[75] Inventors: J. Robert Lemon, Charlotte; William T. Evans; Robert E. Christian, both of Batesville, all of Ark.; Herbert I. Bader, Sharon, Mass.

[73] Assignee: Professional Dental Technologies, Inc., Batesville, Ark.

[21] Appl. No.: 603,638

[22] Filed: Oct. 25, 1990

[51] Int. Cl.⁵ .............................................. A61C 19/04
[52] U.S. Cl. ........................................ 433/72; 33/514
[58] Field of Search ........................ 433/72, 75, 141; 33/514

[56] References Cited

U.S. PATENT DOCUMENTS

| | | | |
|---|---|---|---|
| 1,501,170 | 7/1924 | Korb | 433/72 X |
| 4,182,312 | 1/1980 | Mushabac | 33/514 X |
| 4,203,223 | 5/1980 | Lautenschlager et al. | 433/75 |
| 4,364,730 | 12/1982 | Axelsson | 433/141 |
| 4,445,857 | 5/1984 | Borst | 433/75 |
| 4,501,555 | 2/1985 | Ditchburn | 433/29 |
| 4,552,531 | 11/1985 | Martin | 433/147 |
| 4,768,952 | 9/1988 | Lowenthal | 433/72 |
| 4,791,940 | 12/1988 | Hirschfeld et al. | 433/72 X |
| 4,886,454 | 12/1989 | Lowenthal et al. | 433/72 |
| 5,000,683 | 3/1991 | Brock | 433/141 X |
| 5,022,856 | 6/1991 | Zimble | 433/72 |

FOREIGN PATENT DOCUMENTS

| | | | |
|---|---|---|---|
| 0002904 | 7/1979 | European Pat. Off. | 433/141 |
| 0061218 | 5/1982 | European Pat. Off. | |
| 3411366 | 10/1985 | Fed. Rep. of Germany | |
| 7417962 | 4/1973 | France | |
| 2086232 | 10/1981 | United Kingdom | |
| 88/04159 | 6/1988 | World Int. Prop. O. | 433/72 |

Primary Examiner—John G. Weiss
Assistant Examiner—Nicholas D. Lucchesi
Attorney, Agent, or Firm—William J. Sapone

[57] ABSTRACT

A constant pressure periodontal probe (1) has a probing portion (3) and is connected to a handle (2) through a flexing joint (10). A backing portion (4) extends from the handle adjacent to but spaced away from the probe tip such that a gap (17) exists between the probing portion and the backing portion. As the probing portion is inserted into a pocket between the tooth and gum, the amount of resistance causes the probe portion to be displaced about the flexible joint, closing the gap between the probing and backing portions. When the probing portion contacts the backing portion, a constant insertion pressure has been reached and a reading is taken to determine the depth of the pocket. Utilizing such a constant pressure periodontal probe assures that each reading is taken at a set pressure, preventing damage to the gum tissue and assuring accurate readings.

8 Claims, 2 Drawing Sheets

CONSTANT PRESSURE PERIODONTAL PROBE

TECHNICAL FIELD

This invention relates to periodontal probes and more particularly to a constant pressure periodontal probe which indicates when a desired insertion pressure is achieved.

BACKGROUND OF INVENTION

Periodontal probes are used to test the depth of a pocket which exists between a tooth and a gum. The pocket is formed as a result of progressive gingival inflammation. Once formed, the periodontal pocket provides a sheltered environment for pathogenic microbial colonies, which may cause further connective tissue destruction. The depth measurement indicates whether periodontal disease is present and to what extent; the deeper the pocket, the less attachment there is between the tooth and gum and more likely it is that treatment is required.

Typical periodontal probes, shown for example in U.S. Pat. Nos. 4,768,952, 4,886,454, and 4,764,114, use a needle-like tip. The tip is inserted until the bottom of the pocket is reached, with the tester relying on the resistance to insertion to feel the bottom of the pocket. The tip usually has markings to indicate the depth of the pocket. Pocket depths over about three millimeters indicate that treatment should be undertaken. Two or three readings may be taken per tooth and a history developed to note changes in pocket depth to determine if progressive pocket enlargement is apparent.

A problem with periodontal probing is that, to be accurate, the pressure used to push down the probe tip into the pocket must be the same for each test. In addition, the force applied must be less than would cause the tip to pierce the pocket, damaging the tissue and giving an erroneous reading. If different pressure is applied at different locations or during subsequent probing, the readings will vary and the test results become meaningless.

The World Health Organization has determined that a pressure of about 20 grams should be used as the standard insertion pressure. This is the level at which the probe overcomes the resistance caused by the gum mating with the tooth, yet prevents the probe tip from piercing the bottom of the periodontal pocket. This is a very low value compared to the amount of pressure which could be applied during insertion and it is very difficult to feel when that level of pressure has been reached. By monitoring probing done during a typical examination, it was determined that testers routinely applied double or triple this amount of force without being aware of it.

DISCLOSURE OF THE INVENTION

It is an object of the present invention to provide a constant pressure periodontal probe which provides an easily identifiable indication that a desired insertion force has been applied.

It is another object to provided a constant pressure periodontal probe which is disposable.

It is yet another object to provide a constant pressure periodontal probe which is integrally molded to minimize cost.

These and other objects of the present invention are achieved by providing a periodontal probe having a handle, a probing portion extending from an end of the handle, and a backing portion, extending from the end of the handle adjacent to but spaced away from the probe portion. The probing portion has a needle-like probing tip which may optionally including markings to indicate depth of insertion. This tip is connected to the handle through a flexible joint, preferably shaped and tapered to allow the tip and arm to flex in an arc about the joint as the resistance to insertion increases. The backing portion is separated from the probing portion by a gap, the backing portion providing a stop to limit the travel of the probing portion. The gap is of sufficient width such that when the portions touch, a desired constant pressure is indicated. At that point, the tester reads the depth of insertion. Such a probe assures that an accurate reading is taken, and that all subsequent tests are taken at the same insertion pressure.

DETAILED DESCRIPTION OF THE INVENTION

Figure 1:
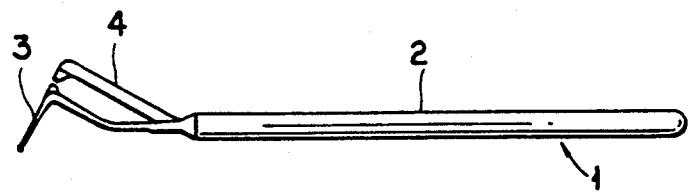
FIG. 1 is a side view of the constant pressure probe of the present invention.

Referring to FIG. 1, a constant pressure probe 1 has a handle 2, a probing portion 3 and a backing portion 4. The handle may be round or shaped to provide effective hand manipulation of the probe.

The probe is made of plastic or metal, with plastic preferred as it allows the probe to be disposable. Among the materials of construction useable with the present invention are polyethylene, polypropylene, nylon, polystyrene, polyurethane, polyetherimid (Ultem TM), steel, stainless steel, or combinations thereof. Ultem TM is preferred as it has good strength properties while being sufficiently high temperature resistant to allow sterilization.

Figure 2:
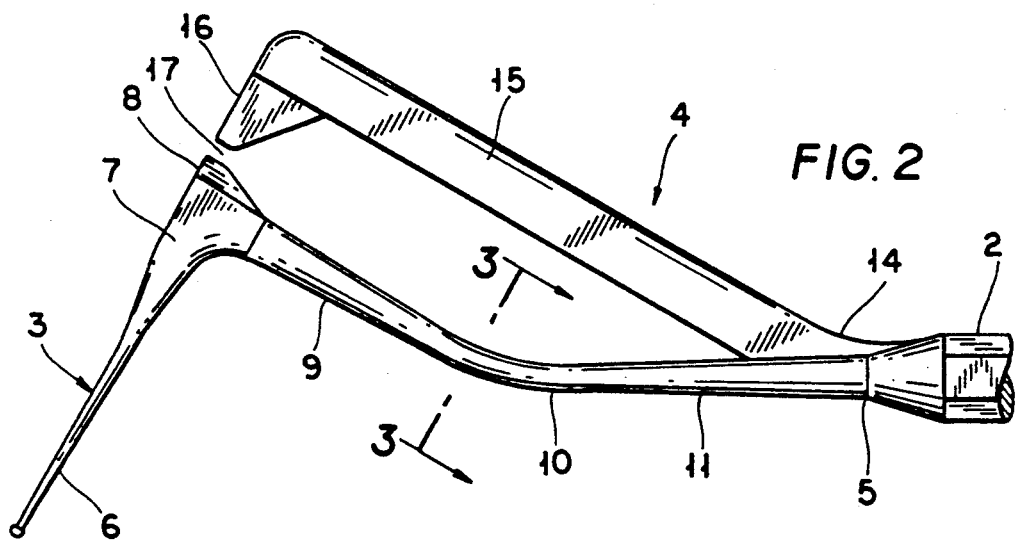
FIG. 2 is an enlarged sectional view of the probe of FIG. 1.

Referring to FIG. 2, the probing portion 3 is joined at junction 5 to the handle 2. The probing portion 3 includes a needle-like tip 6 which extends from a corner 7. The corner 7 has an upwardly extending projection 8, and is attached through a first rigid section 9 to a flexing joint 10 through a second rigid section 11 to the junction 5. The flexing joint 10 provides a focal point for probe displacement when resistance to insertion is met. The flexing joint 10 is tapered and shaped to provide the weakest point between the sections 9 and 11 such that the resistance to probing causes the probe to travel in an arc about the flexing joint.

Figure 3:
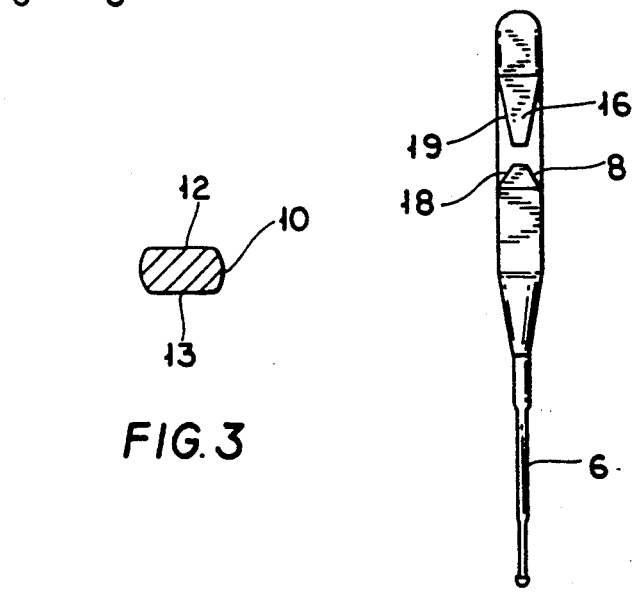
FIG. 3 is a cross sectional view of the probe taken along line 3—3 of FIG. 2.

Referring to FIG. 3, a cross sectional view of the flexing joint 10 is shown. The flexing joint has two opposed flat surfaces 12 and 13, in the desired plane of travel, with the joint having rounded sides to provide a somewhat oblong shape. The flat surfaces provide weakening areas to assure movement in a planar direction in alignment with the backing portion. This guides the probe to prevent displacement in an angular direction, to assure contact with the backing portion. The flexing joint should be made of a resilient material to provide return of the probing portion to its original position after withdrawl. Where a somewhat inelastic material is used, spring means may be incorporated between the portions to bias them apart. Of course, other shapes and designs could be use to provide the flexing joint, and to allow for return of the probing portion to its original position.

Referring again to FIG. 2, the backing portion 4 is joined at an end 14 through the junction 5 to the handle 2. The backing portion 4 has a rigid arm 15 extending parallel to the first section 9 of the probing portion, extending adjacent to but spaced away from the probing portion. Both portions are coplanar and in alignment. The arm 15 has sufficient rigidity to prevent movement when a force greater than the desired probing insertion force is applied against it. This rigidity can be adjusted by increasing the thickness of the arm relative to the thickness of the probing portion. The backing portion has a tip 16 which is spaced a way from the projection 8 of the probing portion, to provide a gap 17 therebetween. The gap 17 is sized to accommodate movement of the probing portion 3 as the resistance to insertion causes the probing portion to move about the joint 10, with contact between the projection 8 and the tip 16 indicating that the desired pressure has been reached. The backing tip 16 provides a stop for receiving the projection 8.

Figure 4:
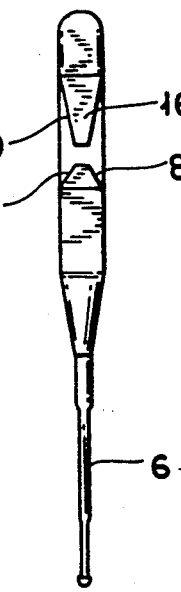
FIG. 4 is an enlarged front view of the probe of FIG. 1.

Referring to FIG. 4, the projection 8 and tip 16 have tapered sides 18 and 19 respectively. In the event that additional probing force is desired, after contact, the user may slightly twist the handle 2 to flex the probing portion in an angular direction about the joint 10 and misalign the tip and projection to allow the projection 8 to bypass the tip 16 and increase the insertion pressure. Depending on the choice of material, as the amount of flexing increases, the resistance to the displacement of the probe about the flexible joint increases, with the modulus and cross-section of the flexing joint determining the maximum amount of displacement allowable.

Figure 5:
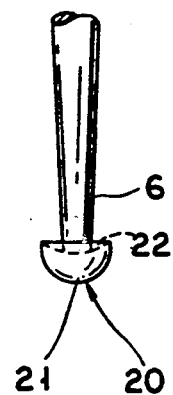
FIG. 5 is an enlarged cross sectional view of the end of the probe tip.

Referring to FIG. 5, the probing tip 6 has a ball end 20 which comprises a partial sphere 21 with an inwardly curved edge 22. The roundness of the sphere allows ease of insertion of the tip between the gum and tooth, but on withdrawal, the edge 22 rides against the tooth surface so that the user may detect if a layer of subgingival calculus has built up on the tooth surface. As the edge 22 is pulled across the tooth surface, it may engage the layer, which the user can feel by the halting motion of the probe during withdrawal.

Figure 4A:
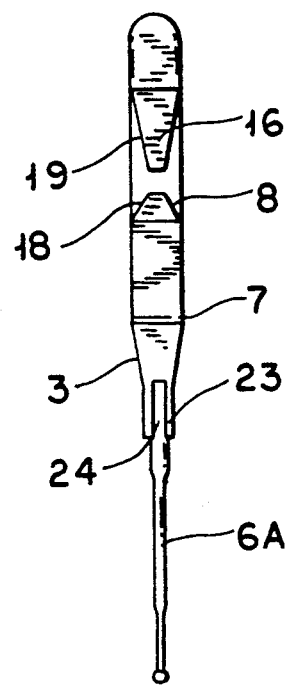
FIG. 4a is an alternative embodiment of the invention.

The probe is preferably produced as a unitary structure to minimize cost and allow mass production by molding. However, it is contemplated that the probe tip may be separately produced and be removable from the corner to allow replacement. For example, as shown in FIG. 4a, the corner 7 may include a channel 23 sized to accept an end 24 of a separable needle-like tip 6a, with suitable means provided for locking the tip in place. Also, where the modulus of the material is insufficient to provide sufficient biasing, spring means could be added to the probe between the portions to assure proper operation. These modifications are all within the scope of the present invention.

While preferred embodiments of the present invention have been shown and described, it will be understood by those skilled in the art that various changes or modifications could be made without varying from the scope of the present invention.

We claim:

1. A constant pressure periodontal probe comprising a handle, a probing portion extending from the handle, and a rigid backing portion extending from the handle adjacent to but spaced away from the probing portion by a gap, a flexing joint provided in the probing portion, the flexing joint being a portion of reduced strength to allow the probing portion to be displaced about the flexing joint as resistance to insertion increases, the backing portion providing a stop to limit displacement of the probing portion, contact between the backing portion and the probing portion indicating that a desired insertion pressure has been reached.

2. The probe of claim 1 wherein the backing portion has a tip for contacting the probing portion.

3. The probe of claim 2 further comprising a partial sphere, disposed on the end of the needle-like tip, an inwardly curved edge provided on the sphere.

4. The probe of claim 1 wherein the probing portion has a needle-like tip, a corner, the needle-like tip extending from the corner, first and second sections disposed on opposite sides of the joint in an angular relationship, the first section connected to the corner and the second section connected to the handle.

5. The probe of claim 4 wherein the corner has a channel, the needle-like tip being locatable in the channel, the needle-like tip being replaceable.

6. The probe of claim 1 wherein the gap between the backing portion and probing portion corresponds to an insertion pressure applied to the probe of 20 grams.

7. The probe of claim 1 wherein the probe is composed of a material from a group consisting essentially of polyethylene, polypropylene, nylon, polystyrene, polyurethane, polyetherimid, and stainless steel.

8. A method for testing for periodontal disease comprising:

providing a periodontal probe having a handle, a probing portion extending from the handle, and a rigid backing portion extending from the handle adjacent to but spaced away from the probing portion by a gap, a flexing joint provided in the probing portion, the flexing joint being an area of reduced strength to allow the probing portion to be displaced about the flexing joint as resistance to insertion increases, the backing portion providing a stop to limit displacement of the probing portion;

inserting the probing portion between the gum and tooth of a patient until the probing portion is displaced in an amount which closes the gap between the backing portion, and the probing portion contact between the backing portion and the probing portion indicating that a desired insertion pressure has been reached; and, determining he depth of insertion when contact is made between the backing portion and the probing portion.

* * * * *